(12) United States Patent
Jung

(10) Patent No.: US 8,415,494 B2
(45) Date of Patent: Apr. 9, 2013

(54) SILYL SUBSTITUTED 1,4-DISILACYCLOHEXANE DERIVATIVES AND PREPARATION METHOD THEREOF

(75) Inventor: Il Nam Jung, Yongin-si (KR)

(73) Assignee: Samsung Fine Chemical Co., Ltd., Ulsan (KR)

( * ) Notice: Subject to any disclaimer, the term of this patent is extended or adjusted under 35 U.S.C. 154(b) by 0 days.

(21) Appl. No.: 12/989,645

(22) PCT Filed: Apr. 21, 2009

(86) PCT No.: PCT/KR2009/002060
§ 371 (c)(1),
(2), (4) Date: Jan. 10, 2011

(87) PCT Pub. No.: WO2009/131347
PCT Pub. Date: Oct. 29, 2009

(65) Prior Publication Data
US 2011/0105777 A1    May 5, 2011

(30) Foreign Application Priority Data

Apr. 25, 2008 (KR) .......................... 10-2008-0038891

(51) Int. Cl.
*C07F 7/08* (2006.01)
(52) U.S. Cl.
USPC ............................ 556/406; 556/400; 556/431
(58) Field of Classification Search .................. None
See application file for complete search history.

(56) References Cited

U.S. PATENT DOCUMENTS

| | | | |
|---|---|---|---|
| 3,553,242 A | | 1/1971 | Fink et al. |
| 4,937,364 A | * | 6/1990 | Okinoshima ............ 556/406 |
| 6,392,077 B1 | * | 5/2002 | Jung et al. ............... 556/481 |

OTHER PUBLICATIONS

Kang, Seung-Hyun et al, "Phosphonium Chloride Induced Dichlorosilylene Transfer from Trichlorosilane," American Chemical Society, *Organometallics* 22(13):2551-2553, May 17, 2003.
Phan, Son Thanh et al, "Platinum-catalyzed double silylations of alkynes with bis(dichlorosilyl)methanes," *Journal of Organometallic Chemistry* 691:604-610, 2006.
Volkova, L.M. et al, "Synthesis of difunctional 1,4-dimethyl-1,4-disilacyclohexanes," *Russian Chemical Bulletin*, 48(9):1712-1716, Sep. 1999.

* cited by examiner

*Primary Examiner* — Sudhakar Katakam
(74) *Attorney, Agent, or Firm* — Seed IP Law Group PLLC

(57) ABSTRACT

The present invention relates to novel 1,4-disilacyclohexane derivatives and a preparation method thereof. More particularly, the present invention provides a method for preparing 1,4-disilacyclohexane derivatives with a hexagonal ring structure at high yield through double silylation of an organosilane compound and a vinyl silane compound having an unsaturated double bond using quaternary organophosphonium salts as a catalyst. According to the present invention, tris(silyl)ethanes having three silyl groups in one molecule can be prepared at the same time and the catalyst can be recovered after reaction. Thus, the method is economical and enables mass-production of 1,4-disilacydohexane derivatives and tris(silyl)ethanes which are precursors of organic/inorganic hybrid materials.

19 Claims, No Drawings

SILYL SUBSTITUTED 1,4-DISILACYCLOHEXANE DERIVATIVES AND PREPARATION METHOD THEREOF

BACKGROUND OF THE INVENTION

1. Field of the Invention

The present invention relates to novel 1,4-disilacyclohexane derivatives and a preparation method thereof, and more particularly, to high efficiency 1,4-disilacyclohexane derivatives obtained through double silylation of an organosilane compound and a vinyl silane compound having an unsaturated to double bond under the presence of quaternary organophosphonium salts.

2. Description of the Related Art

Recently, the inventors of the present application have noticed that when trichlorosilane is reacted to alkene with a carbon-carbon double bond by using a is tetraalkyl phosphonium chloride compound as a catalyst, double silylation in which trichlorosilyl group is included in carbons of both sides of the double bond takes place.

It has been known that this is because a dichlorosilylene (:SiCl$_2$) intermediate created by detaching hydrogen chloride from trichlorosilane (HSiCl$_3$) is added to the double bond to create silacyclopropane, which then reacts with trichlorosilane.

It has been reported that the silylene intermediate is added to carbon-carbon triple bonds to form triangular silacyclopropene and doubling of the silacyclopropene forms 1,4-disilacyclohexene (See Reactive Formula 1).

[Reactive Formula 1]

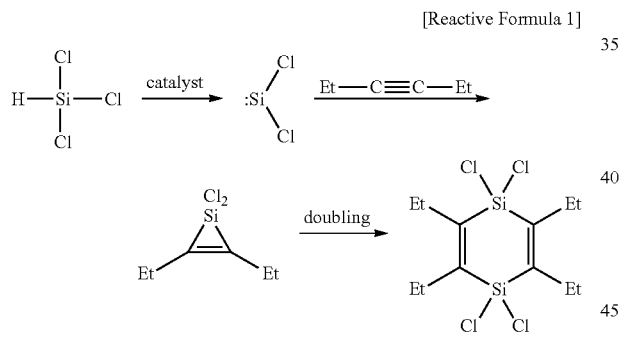

It is believed that silylene, an intermediate, created in this reaction is added to the carbon-carbon triple bonds to form the triangular silacyclopropene, and this unstable silacyclopropene is doubled to create hexagonally annular 1,4-disilacyclohexene.

As for an organosilicic compound such as tris(silyl)ethane, a precursor useful for preparing polycarbosilane or organic/inorganic hybrid material, because the bond of silicon and hydrogen is added to the carbon-carbon double bond of an unsaturated organic compound through the conventional hydrosilylation, only a single silyl group can be introduced, and also because only the precious metal catalyst such as platinum must be used in the reaction, causing the problem in that a preparation cost increases.

In the present invention, by taking a hint from the conventional 1,4-disilacyclohesene preparation process, a method for economically preparing 1,4-disilacyclohexane derivatives, which is useful for preparing polycarbosilane or organic/inorganic hybrid material, with a high production yield has been developed and devised.

Namely, with expectations that the addition of silylene, an intermediate, in the Reactive Formula 1 to the carbon-carbon double bond will create triangular silacyclopropane and doubling of silacyclopropane will create hexagonal 1,4-disilacyclohesane, in the present invention, an organosilane compound and a vinyl silane compound having an unsaturated double bond were reacted under the presence of a quaternary organophosphonium salts-based catalyst, to result in a preparation of novel 1,4-disilacyclohexane derivatives and, at the same time, tris(silyl)ethane together.

SUMMARY OF THE INVENTION

Therefore, an object of the present invention is to provide novel 1,4-disilacyclohexane derivatives, an organosilane compound useful for preparing polycarbosilane or organic/inorganic hybrid material.

Another object of the present invention is to provide a method for to economically preparing the 1,4-disilacyclohexane derivatives with a high production yield.

According to embodiments of the present invention, quaternary organophosphonium salts are used as a catalyst, two silyl groups are introduced to carbon-carbon double bond through double silylation to prepare tris(silyl)ethane having three substituted silyl groups and, at the same time, a hexagonal 1,4-disilacyclohexane compound in which silyl groups are substituted at the positions of 2' and 5' carbons can be synthesized with a high yield. After the reaction, the catalyst layer can be split or when the product is distilled, the catalyst is solidified so as to be easily separated. The quaternary organophosphonium salts can be immobilized (or fixed) to silica or a silicon resin and used thusly, whereby the catalyst can be recovered after being used, so it is very economical and effective for mass-producing precursors of an organic/inorganic hybrid material.

To achieve the above object, there is provided novel 1,4-disilacyclohexane represented by Chemical Formula 1 shown below:

[Chemical Formula 1]

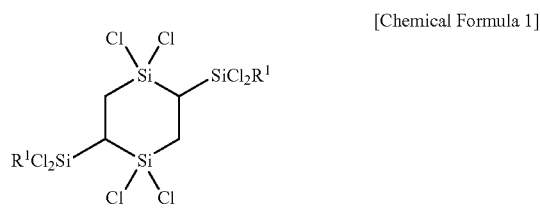

In Chemical Formula 1, R1 is a halogen atom or an alkyl group.

To achieve the above object, there is also provided a method for preparing 1,4-disilacyclohexane represented by Chemical Formula 1, including: reacting an organosilane compound represented by Chemical Formula 2 shown below and a vinyl silane compound represented by Chemical Formula 3 shown below under the presence of quaternary organophosphonium salts.

[Chemical Formula 2]

In Chemical Formula 2, R is a halogen atom or an alkyl group.

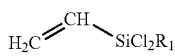

[Chemical Formula 3]

In Chemical Formula 2, R1 is a halogen atom or an alkyl group.

DETAILED DESCRIPTION OF THE INVENTION

The present invention will now be described in detail as follows.

Quaternary organophosphonium salts represented by Chemical Formula 1 according to an exemplary embodiment of the present invention is prepared by allowing an organosilane compound represented by Chemical Formula 2 and a vinyl silane compound having an unsaturated double bond represented by Chemical Formula 3, to double-silylation-react with each other under the presence of quaternary organophosphonium salts. The detail is as represented by Reactive Formula 2 shown below:

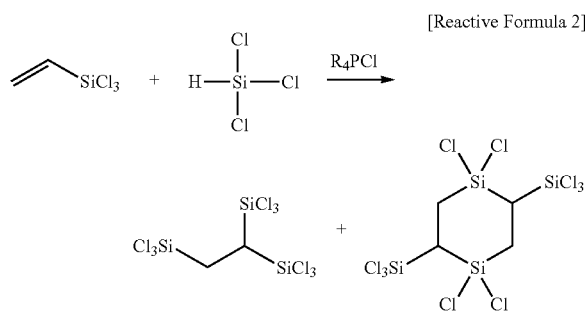

[Reactive Formula 2]

In the organosilane compound represented by Chemical Formula 2, R may be selected from among a halogen atom or a lower alkyl group having 1 to 5 carbons, and preferably, trichlorosilane or methylchlorosilane is selectively used.

In particular, the present invention features the use of the vinyl silane compound having an unsaturated double bond represented by Chemical Formula 3 together with the organosilane compound. In the vinyl silane compound having an unsaturated double bond, R1 may be selected from among a halogen atom or a lower alkyl group having 1 to 5 carbons in Chemical Formula 3, and is vinyltrichlorosilane or vinylmethyldichlorosilane is selectively used.

In particular, only when the compound includes the unsaturated double has the structure in which silicon is directly substituted in the double bond, the hexagonal 1,4-disilacyclohexane according to the present invention can be obtained. Namely, the 1,4-disilacyclohexane having the hexagonal ring structure according to the present invention cannot be obtained only with an alkene compound having a general unsaturated double bond without silicon.

The reaction can be achieved through double silylation different from hydrosilylation, in which both carbons of the unsaturated double bond represented by Chemical Formula 3 are substituted with the organosilane compound represented by Chemical Formula 2. In detail, in the silane compound represented by Chemical Formula 2, silylene intermediate is added to the unsaturated double bond to create silacyclopropane, which is then doubled to generate hexagonal 1,4-disilacyclohexane.

In particular, the present invention features that tris(silyl)ethane represented by Chemical Formula 4, as well as the hexagonal 1,4-disilacyclohexane, can be simultaneously prepared through the double silylation.

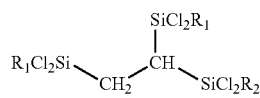

[Chemical Formula 4]

In Chemical Formula 4, R1 and R2, which are the same or different, are a halogen atom or an alkyl group, respectively.

The preparation of the tris(silyl)ethane compound represented by Chemical Formula 4 has been well known, but the use of the quaternary is organophosphonium salt catalyst or its concurrent preparation with the hexagonal 1,4-disilacyclohexane has not been presented nor reported yet.

Meanwhile, in the present invention, preferably, the organosilane compound represented by Chemical Formula 2 is reacted within the range of 1 mol to 8 mol with respect to 1 mol of the vinyl silane compound including the unsaturated double bond represented by Chemical Formula 3.

Also, the quaternary organophosphonium salts can be represented by Chemical Formula 5a or Chemical Formula 5b shown below:

X(R3)$_4$P   [Chemical Formula 5a]

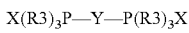

X(R3)$_3$P—Y—P(R3)$_3$X   [Chemical Formula 5b]

wherein X is a halogen atom, R3, which is the same or different, indicates an, alkyl group of $C_1$~$C_{12}$ or —$(CH_2)_n$—$C_6H_5$ (here, n is 0 or 1-6), two R3s can be covalently bonded to form 4-atom rings or 8-atom rings, and Y is an alkylene group of $C_1$~$C_{12}$.

The catalyst is used within the range of 0.05 mol to 0.5 mol with respect to 1 mol of the vinyl silane compound represented by Chemical Formula 3, and to preferably, the catalyst is used within the range of 0.05 mol to 0.2 mol.

Preferably, the double silylation is performed within a temperature range of 10° C. to 250° C. Also, preferably, the double silylation is reacted without a reaction solvent, and selectively, it may be performed under the presence of an aromatic hydrocarbon solvent of one or more selected from the group consisting of is benzene, toluene, and xylene.

The method of simultaneously synthesizing the hexagonal 1,4-disilacyclohexane and 1,1,2-tris(silyl)ethane through double silylation of a vinyl silane compound having an unsaturated double bond and an organosilane compound by using quaternary organophosphonium salts as a catalyst is a novel method which has not been known yet, and 1,4-disilacyclohexane in which silyl groups are substituted at the positions of 2' and 5' carbons is a novel compound.

Meanwhile, as a catalyst according to the present invention, the quaternary organophosphonium salt compound represented by Chemical Formula 5a or 5b may be directly used, or a catalyst immobilized in one or more carriers selected from the group constituting of a silicon resin, silica, inorganic complexing agent, and an organic polymer. For example, the silicon resin has a structure including phosphonium salts having a catalyst activity for the silicon resin, like the structure of $(Cl^-Bu_3P^+(CH_2)_3—SiO_{3/2})_n$, and the other carriers have a structure in which phosphonium salts having a catalyst activity is immobilized in the carriers, similarly.

The technique of immobilizing the catalyst in various carriers is not particularly limited but follows the general catalyst immobilization method, and a detailed description thereof will be omitted.

The present invention is directed to a method for simultaneously to synthesizing hexagonal 1,4-disilacyclohexane and tris(silyl)ethane through double silylation of a vinyl silane compound and an organosilane compound having an Si—H bond by using quarternary organophosphonium salts as a catalyst. The used catalyst is a small amount of catalyst of 10% or smaller and can be easily recovered to be re-used. Considering these facts, the present invention can be applicable to a composition of a novel organosilicic compound in a very economical and effective manner, the process can be very easily performed, and a very low manufacturing cost is incurred, and as such, the present invention can be extensively utilized for polymerization including an organosilicic compound or a preparation of an organic/inorganic hybrid material.

The following embodiments will specify the present invention, but the scope of the present invention is not limited thereto.

Embodiment 1: Reaction of vinyltrichlorosilane and trichlorosilane (catalyst: tetrabutylphosphonium chloride)

A reaction vessel formed as a 25 ml stainless steel tube dried in an oven was cooled under the presence of a dried nitrogen gas, in which 3.0 g (0.019 mol) of vinyltrichlorosilane, 7.5 g (0.056 mol) of trichlorosilane, and 0.6 g (0.002 mol) of tetrabutylphosphonium chloride were then put. The entrance of the reaction vessel was hermetically sealed with a stopper, reaction was performed at 180° C. for three hours, and then, a consumption of a starter and a product were checked through a gas chromatography. 3.0 g (yield: 60.6%) of 2,5-bis(trichlorosilyl)-1,1,4,4-tetrachloro-1,4-disilacyclohexane, 1.5 g (yield: 18.3%) of 1,1,2-tris(trichlorosilyl)ethane, and 0.9 g (yield: 16.0%) of 1,2-bis trichlorosilylethane were obtained through vacuum distillation of a reactant. The 1,2-bis trichlorosilylethane was a reaction by-product (or a residual product). Vacuum distillation was performed to remove the by-product at a low temperature and the resultant material was left to drop 2,5-bis(trichlorosilyl)-1,1,4,4-tetrachloro-1,4-disilacyclohexane as a crystal and it was recrystallized in hexane to increase its purity. The obtained product was analyzed by using 300 MHz 1H magnetic resonance.

In 2,5-bis(trichlorosilyl)-1,4-disilacyclohexane: δ1.86 ppm(t,2H), a Si—CH—Si peak was confirmed, and in 2,5-bis(trichlorosilyl)-1,4-disilacyclohexane: 51.61 ppm(d,4H), a Si—CH$_2$—C peak was confirmed.

In 1,1,2-tris(trichlorosilyl)ethane: δ 1.95 ppm(t,1H), a Si—CH—Si peak was confirmed, and in 1,1,2-tris(trichlorosilyl)ethane: δ 2.05 ppm(d,2H), a Si—CH$_2$—C peak was confirmed.

Embodiment 2: Reaction of vinyltrichlorosilane and trichlorosilane (catalyst: tetraethylphosphonium chloride)

In the same manner as that of Embodiment 1, 3.0 g (0.019 mol) of vinyltrichlorosilane, 7.5 g (0.056 mol) of trichlorosilane, and 0.4 g (0.002 mol) of tetraethylphosphonium chloride were put in a 25 ml stainless steel tube and reacted at 180° C. for three hours. The reactant was vacuum-distilled to obtain 3.0 g (yield: 59.7%) of 2,5-bis(trichlorosilyl)-1,1,4,4-tetrachloro-1,4-disilacyclohexane, 1.4 g (yield: 17.3%) of 1,1,2-tris(trichlorosilyl)ethane, and 0.8 g (yield: 14.3%) of 1,2-bis trichlorosilylethane were obtained.

In 2,5-bis(trichlorosilyl)-1,4-disilacyclohexane: δ1.86 ppm(t,2H), a Si—CH—Si peak was confirmed, and in 2,5-bis(trichlorosilyl)-1,4-disilacyclohexane: 51.61 ppm(d,4H), a Si—CH$_2$—C peak was confirmed.

In 1,1,2-tris(trichlorosilyl)ethane: δ 1.95 ppm(t,1H), a Si—CH—Si peak was confirmed, and in 1,1,2-tris(trichlorosilyl)ethane: δ 2.05 ppm(d,2H), a Si—CH$_2$—C peak was confirmed.

Embodiment 3: Reaction of vinyltrichlorosilane and trichlorosilane (catalyst: tetraphenylphosphonium chloride)

In the same manner as that of Embodiment 1, 3.0 g (0.019 mol) of vinyltrichlorosilane, 7.5 g (0.056 mol) of trichlorosilane, and 0.8 g (0.002 mol) of tetraphenylphosphonium chloride were put in a 25 ml stainless steel tube and reacted at 180° C. for six hours. The reactant was vacuum-distilled to obtain 2.7 g (yield: 53.8%) of 2,5-bis(trichlorosilyl)-1,1,4,4-tetrachloro-1,4-disilacyclohexane, 1.1 g (yield: 13.8%) of 1,1,2-tris(trichlorosilyl)ethane, and 0.9 g (yield: 16.0%) of 1,2-bis trichlorosilylethane were obtained.

In 2,5-bis(trichlorosilyl)-1,4-disilacyclohexane: δ1.86 ppm(t,2H), a Si—CH—Si peak was confirmed, and in 2,5-bis(trichlorosilyl)-1,4-disilacyclohexane: δ1.61 ppm(d,4H), a Si—CH$_2$—C peak was confirmed.

In 1,1,2-tris(trichlorosilyl)ethane: δ 1.95 ppm(t,1H), a Si—CH—Si peak was confirmed, and in 1,1,2-tris(trichlorosilyl)ethane: δ 2.05 ppm(d,2H), a Si—CH$_2$—C peak was confirmed.

Embodiment 4: Reaction of vinyltrichlorosilane and trichlorosilane (catalyst: benzyltriphenylphosphonium chloride)

In the same manner as that of Embodiment 1, 3.0 g (0.019 mol) of vinyltrichlorosilane, 7.5 g (0.056 mol) of trichlorosilane, and 0.8 g (0.002 mol) of benzyltriphenylphosphonium chloride were put in a 25 ml stainless steel tube and reacted at 180° C. for four hours. The reactant was vacuum-distilled to obtain 3.2 g (yield: 63.8%) of 2,5-bis(trichlorosilyl)-1,1,4,4-tetrachloro-1,4-disilacyclohexane, 1.2 g (yield: 15.2%) of 1,1,2-tris(trichlorosilyl)ethane, and 0.9 g (yield: 15.4%) of 1,2-bis trichlorosilylethane were obtained.

In 2,5-bis(trichlorosilyl)-1,4-disilacyclohexane: δ1.86 ppm(t,2H), a Si—CH—Si peak was confirmed, and in 2,5-bis(trichlorosilyl)-1,4-disilacyclohexane: δ1.61 ppm(d,4H), a Si—CH$_2$—C peak was confirmed.

In 1,1,2-tris(trichlorosilyl)ethane: δ 1.95 ppm(t,1H), a Si—CH—Si peak was confirmed, and in 1,1,2-tris(trichlorosilyl)ethane: δ 2.05 ppm(d, 2H), a Si—CH$_2$—C is peak was confirmed.

Embodiment 5: Reaction of vinyltrichlorosilane and trichlorosilane (catalyst: benzyltriphenylphosphonium chloride)

In the same manner as that of Embodiment 1, 3.0 g (0.019 mol) of vinyltrichlorosilane, 7.5 g (0.056 mol) of trichlorosilane, and 0.7 g (0.002 mol) of benzyltributylphosphonium chloride were put in a 25 ml stainless steel tube and reacted at 180° C. for four hours. The reactant was vacuum-distilled to obtain 3.1 g (yield: 62.3%) of 2,5-bis(trichlorosilyl)-1,1,4,4-tetrachloro-1,4-disilacyclohexane, 1.3 g (yield: 16.2%) of 1,1,2-tris(trichlorosilyl)ethane, and 0.8 g (yield: 14.7%) of 1,2-bis trichlorosilylethane were obtained.

In 2,5-bis(trichlorosilyl)-1,4-disilacyclohexane: δ1.86 ppm(t,2H), a Si—CH—Si peak was confirmed, and in 2,5-bis(trichlorosilyl)-1,4-disilacyclohexane: δ1.61 ppm(d,4H), a Si—CH$_2$—C peak was confirmed.

In 1,1,2-tris(trichlorosilyl)ethane: δ 1.95 ppm(t,1H), a Si—CH—Si peak was confirmed, and in 1,1,2-tris(trichlorosilyl)ethane: δ 2.05 ppm(d,2H), a Si—CH$_2$—C peak was confirmed.

Embodiment 6: Reaction of vinyltrichlorosilane and trichlorosilane (catalyst: catalyst obtained by immobilizing {3-(tributylphosphonium)propyl}chloride in silicon resin carrier)

In the same manner as that of Embodiment 1, 3.0 g (0.019 mol) of vinyltrichlorosilane, 7.5 g (0.056 mol) of trichlorosilane, and 1.1 g of silicon resin [$(RSiO_{3/2})n$, R={3-(tributylphosphonium)propyl}chloride] were put in a 25 ml stainless steel tube and reacted at 180° C. for twelve hours. The reactant was vacuum-distilled to obtain 2.3 g (yield: 47.3%) of 2,5-bis(trichlorosilyl)-1,1,4,4-tetrachloro-1,4-disilacyclohexane, 1.8 g (yield: 21.8%) of 1,1,2-tris(trichlorosilyl)ethane, and 0.8 g (yield: 14.3%) of 1,2-bis trichlorosilylethane were obtained.

In 2,5-bis(trichlorosilyl)-1,4-disilacyclohexane: ξ1.86 ppm(t,2H), a Si—CH—Si peak was confirmed, and in 2,5-bis(trichlorosilyl)-1,4-disilacyclohexane: δ1.61 ppm(d,4H), a Si—CH$_2$—C peak was confirmed.

In 1,1,2-tris(trichlorosilyl)ethane: δ 1.95 ppm(t,1H), a Si—CH—Si peak was confirmed, and in 1,1,2-tris(trichlorosilyl)ethane: δ 2.05 ppm(d, 2H), a Si—CH$_2$—C peak was confirmed.

Embodiment 7: Reaction of vinyltrichlorosilane and methylchlorosilane (catalyst: tetrabutylphosphonium chloride)

In the same manner as that of Embodiment 1, 80 g (0.50 mol) of vinyltrichlorosilane, 171.4 g (1.49 mol) of methyldichlorosilane, and 14.7 g of tetrabutylphosphonium chloride were put in a 500 ml stainless steel tube and reacted at 180° C. for six hours. The reactant was vacuum-distilled to obtain 61.4 g (yield: 51.2%) of 2,5-bis(methyldichlorosilyl)-1,1,4,4-tetrachloro-1,4-disilacyclohexane. The obtained product was analyzed with 300 MHz 1H magnetic resonance.

In 2,5-bis(methyldichlorosilyl)-1,1,4,4-tetrachloro-1,4-disilacyclohexane δ0.97 ppm(s, 6H), a Si—CH$_3$ peak was confirmed, in 2,5-bis(methyldichlorosilyl)-1,1,4,4-tetrachloro-1,4-disilacyclohexane: δ1.57 ppm(t, 2H), a Si—CH—Si peak was confirmed, and in 2,5-bis(methyldichlorosilyl)-1,1,4,4-tetrachloro-1,4-disilacyclohexane: δ1.83 ppm(d, 2H) and in 2,5-bis(methyldichlorosilyl)-1,1,4,4-tetrachloro-1,4-disilacyclohexane: δ1.43 ppm(d, 2H), a Si—CH$_2$—Si peak was confirmed.

Embodiment 8: Reaction of vinylmethyldichlorosilane and trichlorosilane (catalyst: tetrabutylphosphonium chloride)

In the same manner as that of Embodiment 1, 120.0 g (0.86 mol) of vinylmethyldichlorosilane, 172.8 g (1.28 mol) of trichlorosilane, and 20.6 g (0.08 mol) of tetrabutylphosphonium chloride were put in a 500 ml stainless steel tube and reacted at 180° C. for three hours. The reactant was vacuum-distilled to obtain 54.4 g (yield: 25.3%) of 2-methyldichlorosilyl-5-trichlorosilyl-1,1,4,4-tetrachloro-1,4-disilacyclohexane, 18.9 g (yield: 5.3%) of 4,5-bis(trichlorosilyl)-2,2-dichloro-2-silapentane, and 99.1 g (yield: 41.7%) of 1,1,1,4,4-pentachloro-1,4-disilapentane were obtained. The obtained products were analyzed with 300 MHz 1H magnetic resonance.

In 2-methyldichlorosilyl-5-trichlorosilyl-1,1,4,4,-tetrachloro-1,4-disilacyclohexane: δ0.95 ppm(s, 3H), a Si—CH$_3$ peak was confirmed, in 2-methyldichlorosilyl-5-trichlorosilyl-1,1,4,4,-tetrachloro-1,4-disilacyclohexane: δ1.24 ppm(t, 1H), a Me—Si—CH—Si peak was confirmed, in 2-methyldichlorosilyl-5-trichlorosilyl-1,1,4,4,-tetrachloro-1,4-disilacyclohexane: δ1.80 pprn(t, 1H), a Cl$_3$Si—CH—Si peak was obtained, and in 2-methyldichlorosilyl-5-trichlorosilyl-1,1,4,4,-tetrachloro-1,4-disilacyclohexane: δ1.52 ppm(d, 4H), a C—CH$_2$—Si peak was obtained.

In 4,5-bis(trichlorosilyl)-2,2-dichloro-2-silapentane: δ1.61 ppm(t, 1H), a Si—CH—Si peak was confirmed, in 4,5-bis(trichlorosilyl)-2,2-dichloro-2-silapentane: δ1.55 ppm(d, 2H), a Si—CH$_2$—Si peak was confirmed, and In 4,5-bis(trichlorosilyl)-2,2-dichloro-2-silapentane: δ 0.96 ppm(s, 3H), a CH$_3$—Si—CH peak was confirmed.

In 1,1,1,4,4-pentachloro-1,4-disilapentane: δ 1.43 ppm(t, 2H), a Cl$_3$Si—CH$_2$—C peak was confirmed, in 1,1,1,4,4-pentachloro-1,4-disilapentane: δ 1.40 ppm(t, 2H), a MeCl$_2$Si—CH$_2$—C peak was confirmed, and in 1,1,1,4,4-pentachloro-1,4-disilapentane: δ 0.92 ppm(s, 3H), a CH$_3$—Si peak was confirmed.

What is claimed is:

1. 1,4-disilacyclohexane represented by Chemical Formula 1 shown below:

[Chemical Formula 1]

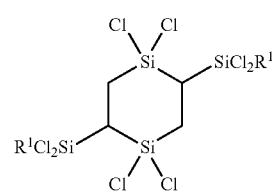

wherein R1 is a halogen atom or an alkyl group.

2. The 1,4-disilacyclohexane of claim 1, wherein the 1,4-disilacyclohexane is prepared from a vinyl silane compound having an unsaturated double bond.

3. A method for preparing 1,4-disilacyclohexane represented by Chemical Formula 1, shown below:

[Chemical Formula 1]

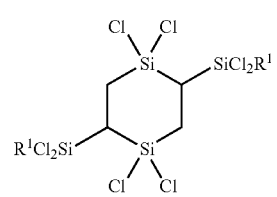

wherein R1 is a halogen atom or an alkl group, comprising:
reacting an organosilane compound represented by Chemical Formula 2 shown below and a vinyl silane compound including an unsaturated double bond represented by Chemical Formula 3 shown below under the presence of quaternary organophosphonium salts:

[Chemical Formula 2]

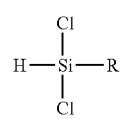

wherein R is a halogen atom or an alkyl group

[Chemical Formula 3]

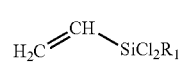

wherein R1 is a halogen atom or an alkyl group.

4. The method of claim 3, wherein tris(silyl)ethane represented by Equation 4 shown below is simultaneously prepared in the reaction:

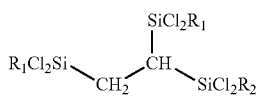
[Chemical Formula 4]

wherein R1 and R2, which are the same or different, are a halogen atom or an alkyl group, respectively.

5. The method of claim 3, wherein the silane compound having the unsaturated double bond has a structure in which silicon is directly substituted in the saturated double bond.

6. The method of claim 3, wherein the organosilane compound represented by Chemical Formula 2 is reacted within the range of 1 mol to 8 mol with respect to 1 mol of the vinyl silane compound including the unsaturated double bond represented by Chemical Formula 3.

7. The method of claim 3, wherein quaternary organophosphonium salt catalyst is a compound represented by Chemical Formula 5a or Chemical Formula 5b shown below:

 [Chemical Formula 5a]

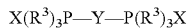 [Chemical Formula 5b]

wherein X is a halogen atom, R3, which is the same or different, indicates an alkyl group of $C_1$~$C_{12}$ or —$(CH_2)_n$—$C_6H_5$ (here, n is 0 or 1~6), two R3s can be covalently bonded to form 4-atom or 8-atom rings, and Y is an alkylene group of $C_1$~$C_{12}$.

8. The method of claim 3, wherein the catalyst has a structure in which the catalyst is immobilized in one or more carriers selected from the group constituting of a silicon resin, silica, inorganic complexing agent, and an organic polymer.

9. The method of claim 3, wherein the catalyst is included within the range of 0.05 mol to 0.5 mol with respect to 1 mol of the vinyl silane compound represented by Chemical Formula 3.

10. The method of claim 3, wherein the reaction is performed as double silylation.

11. The method of claim 3, wherein the reaction is performed within a temperature range of 10° C. to 250° C.

12. The method of claim 3, wherein the double silylation is performed without a reaction solvent or under the presence of an aromatic hydrocarbon solvent.

13. The method of claim 4, wherein the double silylation is performed without a reaction solvent or under the presence of an aromatic hydrocarbon solvent.

14. The method of claim 5, wherein the double silylation is performed without a reaction solvent or under the presence of an aromatic hydrocarbon solvent.

15. The method of claim 6, wherein the double silylation is performed without a reaction solvent or under the presence of an aromatic hydrocarbon solvent.

16. The method of claim 7, wherein the double silylation is performed without a reaction solvent or under the presence of an aromatic hydrocarbon solvent.

17. The method of claim 8, wherein the double silylation is performed without a reaction solvent or under the presence of an aromatic hydrocarbon solvent.

18. The method of claim 9, wherein the double silylation is performed without a reaction solvent or under the presence of an aromatic hydrocarbon solvent.

19. The method of claim 10, wherein the double silylation is performed without a reaction solvent or under the presence of an aromatic hydrocarbon solvent.

* * * * *